(12) United States Patent
Lin et al.

(10) Patent No.: US 12,290,027 B2
(45) Date of Patent: May 6, 2025

(54) METHOD FOR IMPROVING CADMIUM TOLERANCE IN RICE AND REDUCING CADMIUM CONTENT IN RICE GRAINS

(71) Applicant: ZHEJIANG ACADEMY OF AGRICULTURAL SCIENCES, Hangzhou (CN)

(72) Inventors: Fucheng Lin, Hangzhou (CN); Zhenzhu Su, Hangzhou (CN); Lin Li, Hangzhou (CN); Yan Liang, Hangzhou (CN); Kunlun Shen, Hangzhou (CN)

(73) Assignee: ZHEJIANG ACADEMY OF AGRICULTURAL SCIENCES, Hangzhou (CN)

( * ) Notice: Subject to any disclaimer, the term of this patent is extended or adjusted under 35 U.S.C. 154(b) by 470 days.

(21) Appl. No.: 17/833,489

(22) Filed: Jun. 6, 2022

(65) Prior Publication Data
US 2022/0386541 A1 Dec. 8, 2022

(30) Foreign Application Priority Data
Jun. 7, 2021 (CN) .......................... 202110631868.1

(51) Int. Cl.
| | |
|---|---|
| *A01H 1/06* | (2006.01) |
| *A01C 1/06* | (2006.01) |
| *A01G 22/22* | (2018.01) |
| *A01H 17/00* | (2006.01) |
| *C12R 1/645* | (2006.01) |

(52) U.S. Cl.
CPC ................ *A01G 22/22* (2018.02); *A01C 1/06* (2013.01); *A01H 17/00* (2013.01); *C12R 2001/645* (2021.05)

(58) Field of Classification Search
None
See application file for complete search history.

(56) References Cited

FOREIGN PATENT DOCUMENTS

| | | | |
|---|---|---|---|
| CN | 101486970 | * | 7/2009 |
| CN | 103865806 | * | 6/2014 |
| CN | 103865806 A | | 6/2014 |

* cited by examiner

*Primary Examiner* — Medina A Ibrahim
(74) *Attorney, Agent, or Firm* — Jiwen Chen; Joywin IP Law PLLC

(57) ABSTRACT

The present invention discloses a method for improving cadmium tolerance in rice and reducing cadmium content in rice grains, and belongs to the technical field of microbial applications. In the present invention, an endophytic fungi *Falciphora oryzae* FO-R20 with a deposit number of CCTCC M 2021505 is subjected to seedling co-raising with rice in a fungal fertilizer form, the endophytic fungi *Falciphora oryzae* FO-R20 is colonized in the root tissue of rice, and then the rice seedlings are transplanted to a field until harvest. Therefore, the tolerance of rice to cadmium is improved, the content of heavy metal cadmium in the grains of rice is reduced by 12.61%. The FO-R20 has great value by popularization and application in guaranteeing plant health and improving crop quality.

7 Claims, 8 Drawing Sheets

Specification includes a Sequence Listing.

METHOD FOR IMPROVING CADMIUM TOLERANCE IN RICE AND REDUCING CADMIUM CONTENT IN RICE GRAINS

This application claims priority to Chinese Patent Application No. 2021106318681 filed Jun. 7, 2021, which is hereby incorporated by reference.

FIELD OF TECHNOLOGY

The present invention relates to the technical field of microbial applications, and particularly relates to a method of using *Falciphora oryzae* FO-R20 for improving cadmium tolerance in rice and reduction of cadmium content in rice grains.

BACKGROUND TECHNOLOGY

With the rapid development of industrial, urbanization and agricultural intensive production in China, the problem of heavy metal pollution in farmland is increasingly serious, which seriously threatens the quality safety of grains and human health. The problem of excessive cadmium in rice is extremely severe, and how to reduce the cadmium accumulation in rice has attracted much attention. There is an urgently need to find an environment-friendly, ecological, safe, efficient, economical and generalizable countermeasure to solve the problem of cadmium accumulation in rice.

In recent years, mycologists and ecologists have paid attention to the application of endophytic fungi in plant stress resistance, especially in heavy metal stress resistance. In 1989, Buttrey performed a study and found that endophytic fungi (*Acremonium coenophialum*) could reduce the copper content in tall fescue (Buttrey, 1989), and thus the effect of endophytic fungi on tolerance of host to heavy metal was discovered. The grass endophytic fungi *Epichloë/Neotyphodium* could enhance the tolerance (Zaurov et al., 2001) of the fine fescue on heavy metal aluminum. Besides inducing the host plants to improve the tolerance to heavy metal (Shi et al., 2017), the endophytic fungi also had good biological adsorption and heavy metal fixing capabilities. The maximum adsorption capacity of an endophytic fungi strain *Microsphaeropsios* sp. isolated from cadmium hyperaccumulator *Solanum nigrum* L on cadmium reached 247.5 mg·kg$^{-1}$, which was stronger than the adsorption capacity of any activated carbon or other adsorbents (Xiao et al., 2010). The endophytic fungi had a metal isolation and chelation system which could improve the tolerance of the host plants to the heavy metals (Aly et al., 2011). Many fungus could survive in a high-concentration heavy metal environment due to their some unique tolerance mechanisms, such as isolation and chelation of extracellular heavy metals, binding of the heavy metals on cell walls, intracellular isolation and complexation, and compartmentation (Fomina et al., 2005). Therefore, the biotechnology of "improving quality and efficiency" for the plants using the endophytic fungi can also become a new driving means which is very compatible with the traditional stress resistance breeding and transgenic technology cultivation, and it has a broad application prospect.

The invention patent under the application number of CN201410068912.2 disclosed an application of a fungal strain *Phialophora oryzae* with a deposit number of CGMCC No. 2737 in reduction of heavy metal cadmium in tobacco. However, there is no report yet so far of applying the wild rice endophytic fungi in rice to improve stress resistance of the rice to heavy metal cadmium.

SUMMARY OF THE INVENTION

An objective of the present invention is to provide an endophytic fungi strain capable of improving cadmium tolerance of rice and reducing cadmium content in grains of rice, so as to solve the problem of cadmium accumulation in the rice.

To achieve the above object, the following technical solution is adopted herein.

In the present invention, a new endophytic fungi of *Phialophora* was isolated and obtained from the root system of *Oryza meyeriana* in Yunnan, the strain was identified as belonging to the genus *Phialophora* in the family Magnaporthaceae in the class Sordariomycetes in the phylum Ascomycota in the kingdom Fungi, and was designated with the scientific name *Falciphora oryzae* FO-R20. The strain was deposited on May 8, 2021 in the China Center for Type Culture Collection (CCTCC) at Wuhan University in Wuhan, China, the recognized IDA under the Budapest Treaty on the International Recognition of the Deposit of Microorganisms for the Purposes of Patent Procedure, under the deposit number of CCTCC M 2021505, and the scientific name thereof is *Falciphora oryzae*.

It is demonstrated by the study of the present invention that after colonization of the endophytic fungal *Falciphora oryzae* FO-R20 at the root tissues of rice, the tolerance of rice seedlings to cadmium can be remarkably improved.

The present invention provides an application of an endophytic fungi *Falciphora oryzae* FO-R20 with a deposit number of CCTCC M 2021505 in improvement of tolerance of rice to cadmium.

Further, the application comprises the step of co-culturing the endophytic fungi *Falciphora oryzae* FO-R20 and rice seeds to colonize the endophytic fungi *Falciphora oryzae* FO-R20 in the root tissue of rice seedlings.

It is found by the study of the invention that *Falciphora oryzae* FO-R20 is colonized in the root tissue of the rice, and a strain adsorbs heavy metals in own mycelia, so that the accumulation of cadmium in the grains of rice is reduced.

The present invention provides an application of an endophytic fungi *Falciphora oryzae* FO-R20 with a deposit number of CCTCC M 2021505 in reduction of cadmium content in grains of rice.

Further, the application comprises the steps of co-culturing endophytic fungi *Falciphora oryzae* FO-R20 with rice seeds to colonize the endophytic fungi *Falciphora oryzae* FO-R20 in the root tissue of rice.

The present invention further provides a method for improving tolerance of rice to cadmium and reducing cadmium content in grains of rice, comprising the following steps:

(1) inoculating an endophytic fungi *Falciphora oryzae* FO-R20 with a deposit number of CCTCC M 2021505 into a liquid fermentation medium and performing culturing to obtain fermentation broth, and then inoculating the fermentation broth on sterile barley grains and performing culturing in the dark until mycelia grow and the grains are covered with mycelia to obtain an FO-R20 solid fungal fertilizer;

wherein the liquid fermentation medium contains 0.4% of soybean cake flour, 1% of corn flour, 0.05% of magnesium sulfate and 0.1% of dipotassium phosphate per 250 mL of the medium by mass percentage;

(2) mixing the FO-R20 solid fungal fertilizer with a seedling substrate to obtain a mixed substrate, in which germinated rice seeds are sown for seedling raising and culturing to obtain rice seedlings; and (3) transplanting the rice seedlings to a field, and performing culturing until harvest.

Further, in the step (1), before liquid fermentation, the endophytic fungal *Falciphora oryzae* FO-R20 is inoculated in a PDA medium for activated culture and is cultured in dark for 7 days at 25° C.

Further, the fermentation broth and the sterile barley grains are mixed in a ratio of 100 mL:500 g and cultured at 25° C. in the dark until mycelia grow and the grains are covered with mycelia.

Further, in the step (2) of preparing the mixed substrate, the solid fungal fertilizer and the seedling substrate are mixed in a mass ratio of 1:9.

Further, the rice seeds were soaked in 3000-time diluted 25% phenamacril for 2 days for seed disinfection, and then placed in a dark constant-temperature incubator set at 30° C. for 1-2 days to facilitate germination.

The beneficial effects of the present invention are as follows.

In the present invention, the endophytic fungi *Falciphora oryzae* FO-R20 is subjected to seedling co-raising with rice in a fungal fertilizer form, the endophytic fungi *Falciphora oryzae* FO-R20 is colonized in the root tissue of rice, and then the rice seedlings are transplanted to the field until harvest. Therefore, the tolerance of rice to cadmium is improved, the content of heavy metal cadmium in the grains of rice is reduced by 12.61%. The FO-R20 has great value by popularization and application in guaranteeing plant health and improving crop quality.

DESCRIPTION OF THE EMBODIMENTS

Figure 1:
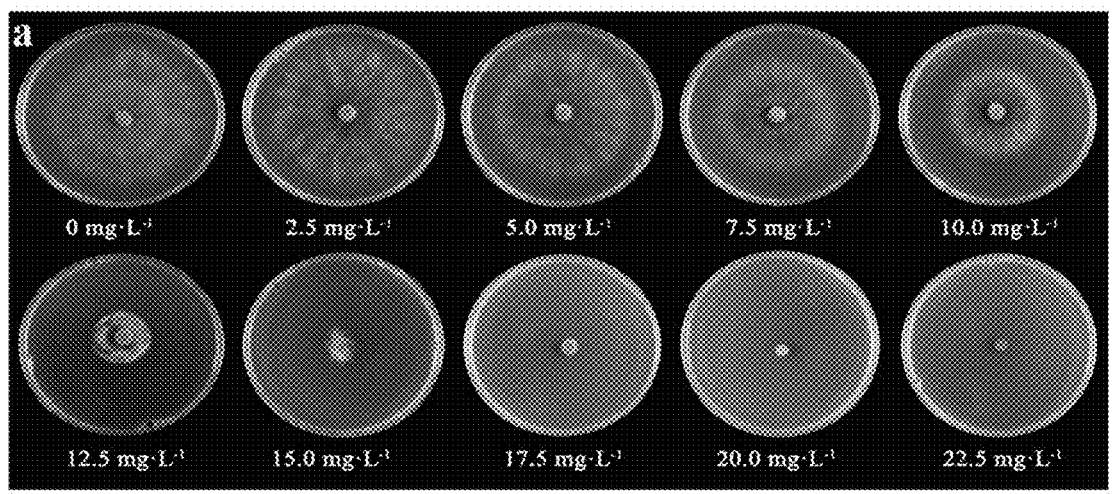
FIG. 1 shows cadmium tolerance test of an FO-R20 strain in Example 2.

The present invention is further described hereinafter in combination with detailed examples, but the present invention is not limited hereto. Unless otherwise specified, the technical means adopted in the examples are all regular technical means in the field, and the reagents are all commercially available.

Example 1 Isolation and Identification of Endophytic Fungal FO-R20

I. Isolation and Purification of Endophytic Fungi FO-R20

The endophytic fungi FO-R20 was isolated from the root system of *Oryza meyeriana* (collected from Xishuangbanna, Yunnan Province, China). The detailed method of isolation was as follows: firstly, the root system of the wide rice was continuously rinsed with tap water and the soil particles and appendages were removed carefully. Healthy root tissues were picked for surface sterilization, and were immersed in 75% ethanol for 1-2 min and 1% sodium hypochlorite for 4-5 min, and subsequently rinsed with sterile deionized water three times. The root tissues were cut into 0.5 cm long segments, which were then transferred into 2% malt extract agar (MEA, malt extract agar, OXOID; with 50 mg/L of chloramphenicol added to the medium to inhibit the growth of endophytic fungi) plates for incubation at 25° C. in the dark. Endopytic fungal mycelia emerged from the edge of the tissue cuts on the fifth day of incubation, and were carefully picked with an inoculation loop and transferred into a fresh PDA medium for purification and cultivation. The strain was recorded as FO-R20.

The PDA medium contained 20 g/L of dextrose, 200 g/L of potatoes and 15 g/L of agar. The potatoes (200 g/L) were weighed according to the volume of the medium to be prepared, and were boiled, mashed, dissolved and filtered, then added with dextrose and agar, and autoclaved at 121° C. for 20 min.

II. Identification of Strain

1. Morphological Identification

The isolated and purified FO-R20 was inoculated on a PDA medium and cultured at 25° C. for 7 days. A small amount of the fungal mass was picked with an inoculation loop to prepare a slide for observation, and measurement under an optical microscope. The morphological characteristics thereof are that, the colony of strain FO-R20 grew slowly on the PDA plate and the colony diameter reached 6 cm after growing on the PDA plate at 25° C. for 10 days; aerial mycelia were poorly developed, prostrating on the medium surface, and the colony was brown, the mycelia were hyaline or dark brown, 1.0-2.5 μm in width; conidiophores were bottle-shaped, solitary, unbranched, 5.0-13.5× 2.5-3.0 μm; conidia were sickle-shaped, colorless, no septum, 7.0-9.0×0.8-1.2 μm.

2. Molecular Identification (1) DNA Extraction

① After the culture of FO-R20 on the PDA plate at 25° C. for 7 days, the mycelia were collected from the plate with a tooth pick and transferred into a sterilized 1.5 mL centrifuge tube containing 300 μL extraction buffer (1 M KCl, 100 mM Tris-HCl, 10 mM EDTA, pH=8.0).

② The fungal mass was pulverized with an electric grinder and vigorously vortexed for 2 min.

③ The mass was centrifuged at 10,000 rpm for 10 min.

④ The supernatant was pipetted to a second clean centrifuge tube, and the precipitate was discarded.

⑤ Isopropanol (AR) was added to the supernatant in an equal volume, and mixed by inverting the tube gently several times, then centrifuged at 12,000 rpm for 10 min to precipitate the nucleic acid.

⑥ The supernatant was discarded gently, and the centrifuge tube containing the precipitate was put on an absorbent paper upside down to drain water.

⑦ Subsequently, 300 μL of 70% ethanol was added and mixed with the precipitate by inverting the tube gently several times and then centrifuged at 12,000 rpm for 2 min.

⑧ The supernatant was discarded gently, and step ⑦ was repeated once.

⑨ The centrifuge tube was placed on an absorbent paper upside down to drain water, and placed at 37° C. for 15 min such that ethanol was fully evaporated.

⑩ The precipitate was resuspended in 50 μL ddH$_2$O to obtain the genomic DNA of FO-R20 with a concentration up to 30 ng/μL.

(2) PCR Amplification of Fungal ITS rDNA Gene

The PCR amplification was performed in a 50 μL reaction system containing: 2 μM each of an upstream primer and a downstream primer, 200 μM of dNTPs, 1.5 mM of MgCl$_2$, 5 μL of 10×PCR buffer, 2 μL of template DNA, and 2 U of Taq enzyme.

The sequence of the upstream primer ITS1 was 5'-TCCGTAGGTGAACCTGCGG-3'(SEQ ID NO: 2), and the sequence of the downstream primer ITS4 was 5'-TCCTCCGCTTATTGATATGC-3'(SEQ ID NO: 3).

The PCR amplification reaction was carried out with a Longgene MG96G PCR cycler. The PCR cycling conditions consisted of: pre-denaturation at 94° C. for 2 min; then 35 cycles of denaturation at 94° C. for 30 sec, annealing at 55° C. for 40 sec and extension at 72° C. for 1 min; and a final extension at 72° C. for 10 min.

(3) Recovery and Purification of PCR Products

After the completion of the PCR reactions, the PCR products were checked by electrophoresis in 1% agarose gel, and then recovered and purified with the DNA gel purification kit of Axygen Biotechnology Limited, following the step-by-step procedure provided in the kit instructions.

(4) Gene Sequencing and Sequence Analysis

The purified and recovered target DNA fragment checked by electrophoresis were delivered to Sangon Biotech (Shanghai) for sequencing with an ABIPRISMA377 automatic sequencer. After strict check of the sequencing result, a DNA fragment sequence as shown in SEQ ID No. 1 with a length of 527 bp was obtained.

Homologous or similar nucleotide sequences were searched for and aligned to the obtained nucleotide sequence by BLAST in the GenBank database on the national center for biotechnology information (NCBI) website. According to the BLAST alignment, the strain was identified as belonging to the genus *Phialophora*, with a percentage coverage of 100% and an identity up to 100% between the obtained sequence and the sequence under accession number NR_153972.1.

As demonstrated by the results of the above molecular identification and morphological identification, the newly isolated strain belongs to the genus *Phialophora* in the family Magnaporthaceae in the class Sordariomycetes in the phylum Ascomycota in the kingdom Fungi. The strain was designated with the scientific name *Falciphora oryzae* FO-R20, and was deposited on May 8, 2021 in the China Center for Type Culture Collection (CCTCC) at Wuhan University in Wuhan, China, the recognized IDA under the Budapest Treaty on the International Recognition of the Deposit of Microorganisms for the Purposes of Patent Procedure, under the deposit number of CCTCC M 2021505.

Example 2 Influence of Endophytic Fungi FO-R20 on Tolerance of Rice to Cadmium Stress Plant: *Oryza sativa* L., variety: C039 used for indoor co-culture; commercial varieties such as Zhejing 88, Yongyou 1540, and Yongyou 538 used for field co-culture.

Heavy metal: cadmium

1. Activated Culture of Strain

FO-R20 preserved on a filter paper sheet was inoculated on a potato dextrose agar (PDA) solid medium to be activated through culturing at 25° C. for 7 days in the dark, and then set aside.

The PDA medium contained 20 g of dextrose, 200 g of potatoes and 15 g of agar per liter medium. The potatoes were weighed according to the volume of the medium to be prepared, and were boiled, mashed, dissolved and filtered, then added with dextrose and agar, and autoclaved at 121° C. for 20 min.

2. Detection of Tolerance of FO-R20 Under Cadmium Concentration Gradient

The concentrations of cadmium ions in the PDA medium were 0 mg·L$^{-1}$, 2.5 mg·L$^{-1}$, 5 mg·L$^{-1}$, 7.5 mg·L$^{-1}$, 10 mg·L$^{-1}$, 12.5 mg·L$^{-1}$, 15 mg·L$^{-1}$, 17.5 mg·L$^{-1}$, 20 mg·L$^{-1}$, 22.5 mg·L$^{-1}$ and 25 mg·L$^{-1}$. FO-R20 segments were inoculated on the PDA medium with different concentration gradients, and cultured for 10 days at 25° C. in the dark.

3. Co-Culture of FO-R20 and Rice Seedlings

After being shelled, CO39 rice seeds were disinfected with 75% ethanol for 10 min, then disinfected with 1% NaClO for 10 min, and finally washed with sterile water. After being disinfected, the seeds were placed on a ½MS medium for germination culture.

When radicles emerged from the seeds, the seeds with consistent growth vigor were selected and placed on the ½MS medium in a test tube with the caliber of 4 cm, wherein three seeds were placed in each tube, and a sterile PDA segment was set as a contrast. Different cadmium concentration gradients were set for the ½MS medium, namely 0 μM, 0.5 μM, 1.25 μM, 2.5 μM, 5 μM and 10 μM respectively. The seeds were cultured in an incubator with 25° C. constant-temperature illumination for 16 hours/8 hours in light/dark.

Remarks: an MS medium (1 L) was prepared from 1,900 mg/L of potassium nitrate, 1,650 mg/L of ammonium nitrate, 370 mg/L of magnesium sulfate, 170 mg/L of monopotassium phosphate, 440 mg/L of calcium chloride, 22.3 mg/L of manganese sulfate, 8.6 mg/L of zinc sulfate, 6.2 mg/L of boric acid, 0.83 mg/L of potassium iodide, 0.25 mg/L of sodium molybdate, 0.025 mg/L of copper sulfate, 0.025 mg/L of cobalt chloride, 27.8 mg/L of ferrous sulfate, 37.3 mg/L of $Na_2EDTA$, 2.0 mg/L of glycine, 0.1 mg/L of thiamine hydrochloride, 0.5 mg/L of pyridoxine hydrochloride, 0.5 mg/L of nicotinic acid, 100 mg/L of inositol, 30 g of cane sugar and 8 g of agar powder; the volume was fixed to 1 L through $H_2O$ was; and the pH was 5.8. The ½ MS medium was the MS medium with a large amount of elements reduced by half and the content of other elements unchanged.

4. Co-Culture of FO-R20 Fungal Fertilizer and Rice Seedlings (1) Preparation of a solid fungal fertilizer: endophytic fungi FO-R20 mycelia segments (with the diameter of 0.5 cm) which were cultured for 7 days were placed into a liquid fermentation medium (the liquid fermentation medium contained 0.4% of soybean cake flour, 1% of corn flour, 0.05% of magnesium sulfate and 0.1% of dipotassium phosphate per 250 mL of the medium) for fermentation culture (at 25° C. and 150 rpm for 7 days). Then fermentation broth was inoculated onto sterilized barley grains (the inoculation amount was 100 mL/500 g), and the barley grains were placed into the incubator for dark culture for 10 days, thus obtaining the FO-R20 solid fungal fertilizer.

(2) Application of solid fungal fertilizer: the fermented solid fungal fertilizer were mixed with a seedling substrate and spread in seedling trays (each seedling tray containing 10 g solid fungal fertilizer). The rice seeds (Yongyou 1540, Yongyou 538, Zhejing 88) were soaked in 3000-time diluted 25% phenamacril for 2 days for seed disinfection, and then placed in a dark constant-temperature incubator set at 30° C. for 1-2 days to facilitate germination. When radicles emerged from the seeds, the seeds were uniformly sown in seedling trays and placed in a seedling field for seedling raising.

(3) Transplanting of rice seedlings: the rice seedlings growing in the trays for about 23-25 days were transplanted to a field and cultured until harvest.

5. Determination of Heavy Metal Cadmium Content

A microwave digestion-inductively coupled plasma mass spectrometry (ICP-MS) method (Dai Qi et al., 2009) was performed. The method comprised the following specific steps: a collected sample was dried at a temperature of 105° C. for 30 min, then dried at a temperature of 65° C. until the weight was constant, and then crushed and sieved (the diameter of each sieve pore was 1 mm). 0.5 g of sieved sample was weighed and placed into a digestion tank, 4 mL of $HNO_3$ (high-grade pure) and 2 mL of $H_2O_2$ were added and stood for 30 min, then a sealing cover was arranged on the digestion tank, the digestion tank was placed into a microwave instrument (an MARS microwave digestion instrument: produced by American CEM) for digestion (a digestion program: the working power was 1,600 W in the first step, the temperature was increased for 5 min to reach 120° C. and then held for 2 min; and the working power was 1,600 W in the second step, the temperature was increased for 8 min to reach 195° C. and then held for 25 min), after the temperature reached room temperature, the digestion tank was placed into a computer temperature control heater for removing acid until the residual acid amount was less than 1 mL; and a digestion solution was transferred to a 25 mL volumetric flask using high-purity water for volume fixing, the digestion solution was clear, light yellow or colorless, and the digestion solution was shaken up for later use; and a reagent blank control was prepared. During measurement, sample solutions were introduced into the ICP-MS (Varian 820 ICP-MS, produced by the American CEM) instrument for measurement respectively, and results were calculated.

6. Result Analysis $Cd^{2+}$ of different concentrations caused significant differences in FO-R20 colony morphology. Under the condition of no cadmium stress, the colony of strain was brown, and mycelia were developed in a prostrating way; as the increase of the concentration of $Cd^{2+}$, the center of the colony was gradually developed into black brown, the edges were white, the colony diameter gradually reduced, and the colony was developed in a radial shape; when the concentration of $Cd^{2+}$ reached 10 $mg·L^{-1}$, the center of the colony of strain was black, and the edges were still white; and when the concentration of $Cd^{2+}$ was increased to 12.5 $mg·L^{-1}$, the whole colony of strain was white, the edges of the colony of strain were neat, and the aerial mycelia were needle-shaped. When the concentration of $Cd^{2+}$ reached 22.5 $mg·L^{-1}$, the growth of the colony of strain was completely inhibited (FIG. 1).

Figure 2:
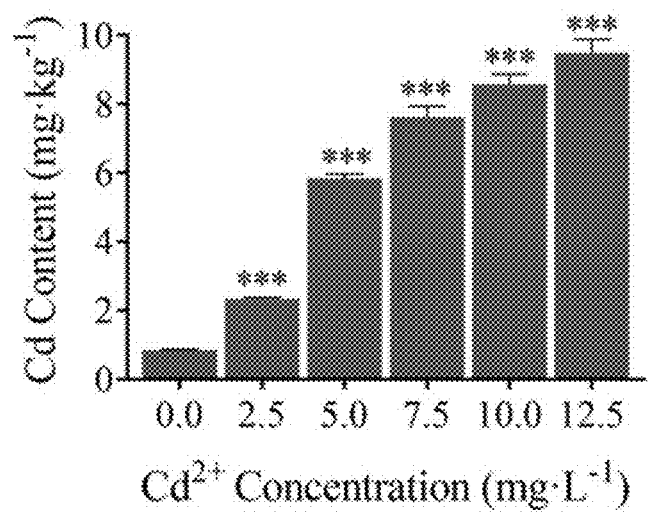
FIG. 2 shows ability of an FO-R20 strain to accumulate cadmium in Example 2. The histogram shows mean±SD. Significance difference (t-test): *** means significance P<0.001.

With the increase of cadmium stress concentration, the diameter of the colony of endophytic fungi FO-R20 was gradually reduced, the growth rate was reduced, but the content of cadmium element in mycelia was gradually increased (FIG. 2).

Figure 3:
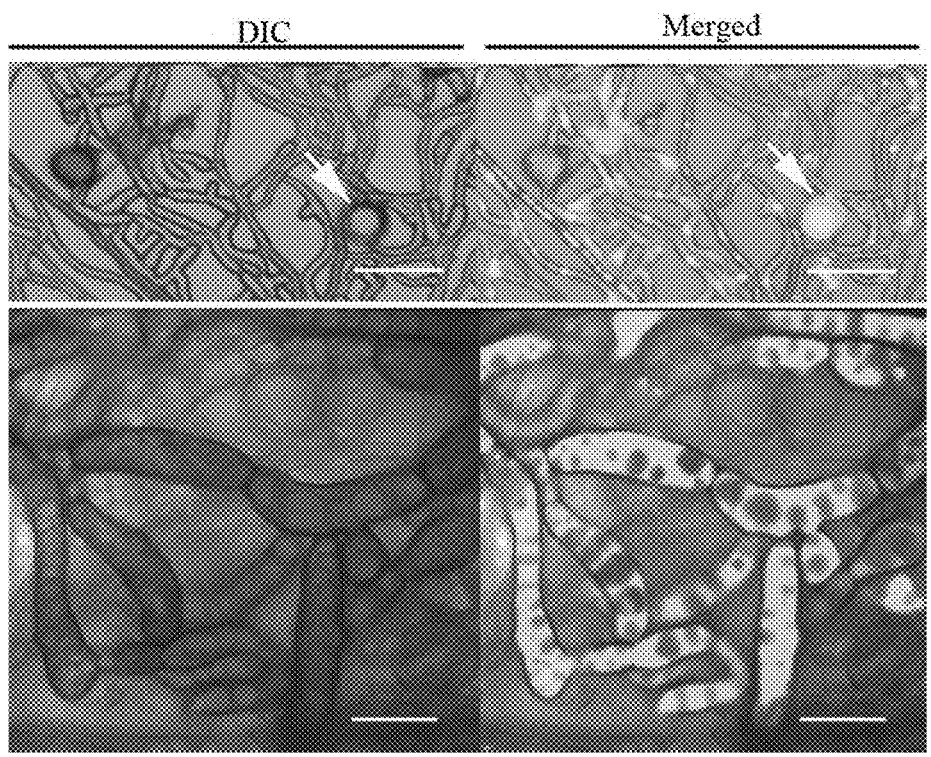
FIG. 3 shows distribution of cadmium ions in FO-R20 mycelial cells in Example 2. Arrows point to chlamydospores. Green fluorescence refers to dyed cadmium ions.

The spatial orientation condition of cadmium elements in FO-R20 mycelia was observed through a cadmium fluorescent dye (Leadmium™ Green AM, Invitrogen, USA), and the observation result showed that a large amount of cadmium elements were accumulated in vacuoles, cell walls and cytoplasm (FIG. 3), which indicated that the main accumulation parts of FO-R20 on heavy metal cadmium were vacuoles, cell walls and cytoplasm; and it was presumed that the vacuoles were the main isolation and detoxification places of FO-R20 heavy metals, and the cell walls and cytoplasm might be rich in substances such as chelatins, amino acids and metallothionein to be complexed with cadmium.

Figure 4:
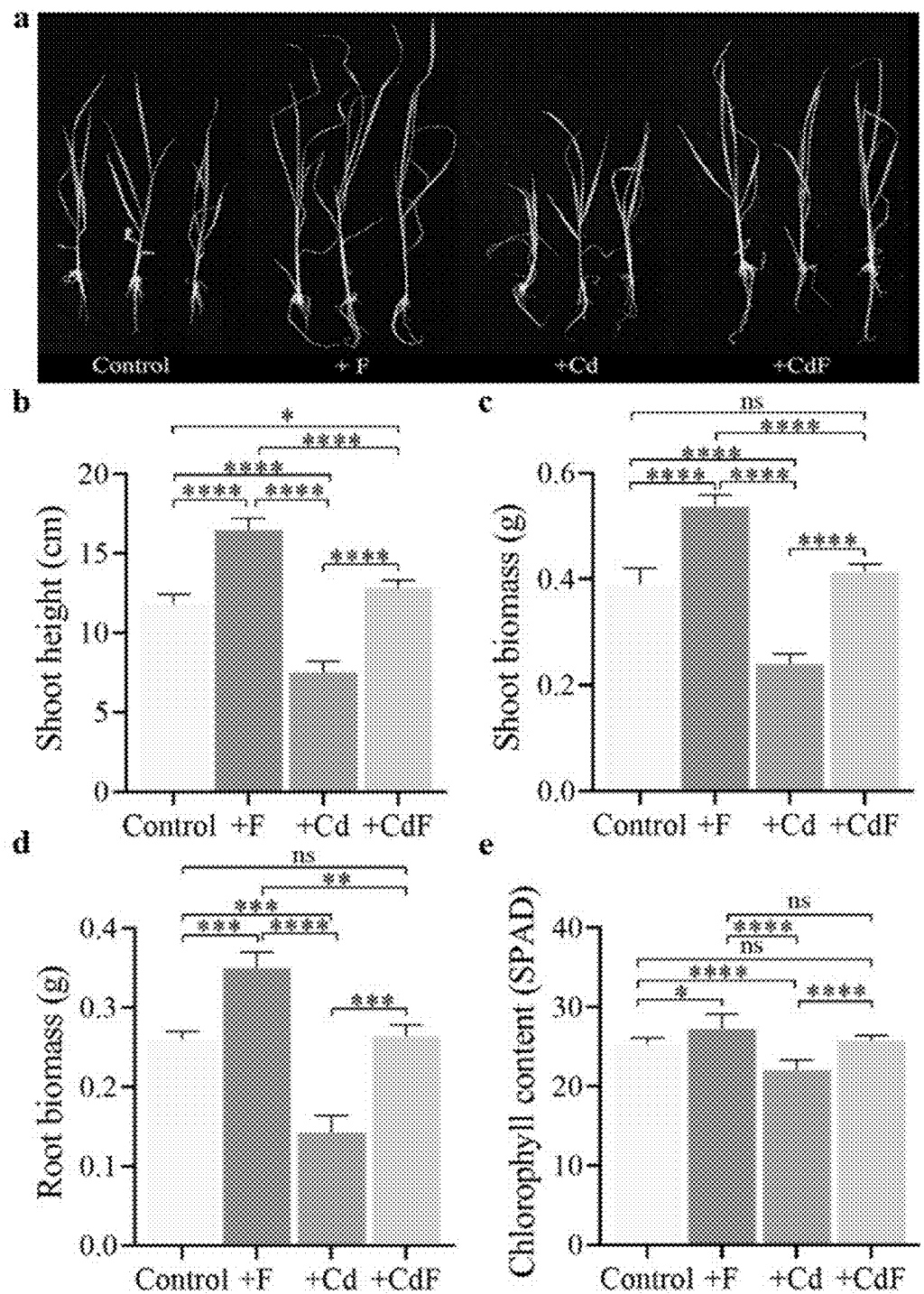
FIG. 4 shows influence of an FO-R20 strain on tolerance of rice seedlings to cadmium in Example 2. (a) Colonization of the FO-R20 strain in the root can improve the tolerance of rice seedlings to cadmium; (b)-(e) Influence of the FO-R20 strain on growth indexes of rice seedlings under cadmium stress. The histogram shows mean±SD, n=9. Significant differences (one-way ANOVA using Tukey's method for multiple comparisons): * means P<0.05,  means P<0.01, * means P<0.001, **** means P<0.0001, ns means no significance. Wherein Control means control, +F means inoculation with FO-R20, +Cd means with treatment with 5 µM cadmium, and +CdF means inoculation with FO-R20 and treatment with 5 µM cadmium.

In a closed culture environment of a test tube, when the cadmium stress concentration was 5 μM (namely 1.2 $mg·kg^{-1}$), the growth of plants (+Cd without being inoculated with FO-R20 was inhibited, the plants were short and small, the leaf tips were withered and yellow, and the root systems were sparse. In contrast, rice plants (+CdF) inoculated with FO-R20 grew well, the symptoms (such as short and small plants and yellowing of leaves) caused by cadmium were relieved, and the plant height, biomass and chlorophyll content were obviously higher than those of a Cd treatment group (FIG. 4).

Figure 5:
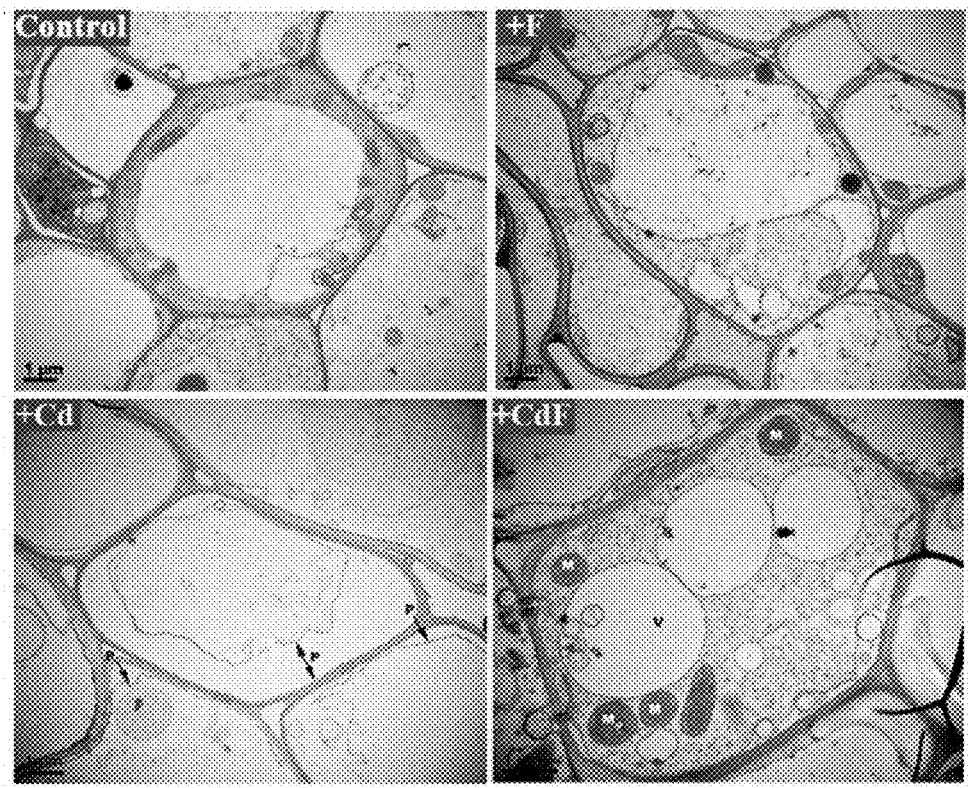
FIG. 5 shows ultrastructures of rice root cells under a transmission electron microscope in Example 2. Control means control, +F means inoculation with FO-R20, +Cd means treatment with 5 µM cadmium, +CdF means inoculation with FO-R20 and treatment with 5 µM cadmium, and P means plasmolysis. Plasmolysis occurs in roots subjected to cadmium treatment, but no plasmolysis occurs in roots inoculated with FO-R20 and subjected to cadmium treatment.

Ultrastructures of rice root cells were observed under a transmission electron microscope. The observation results showed that plasmolysis occurred in roots subjected to cadmium treatment, but no plasmolysis occurred in roots inoculated with FO-R20 and subjected to cadmium treatment (FIG. 5).

Figure 6:
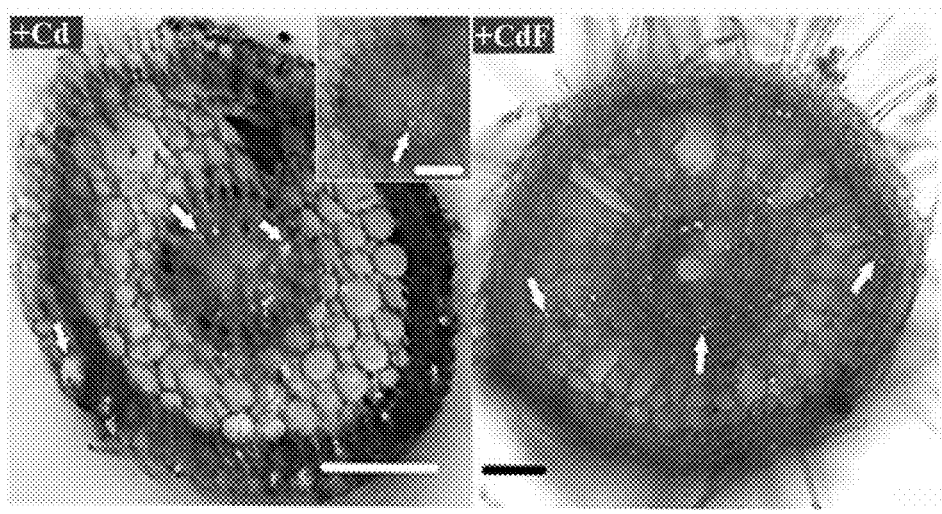
FIG. 6 shows distribution of cadmium ions in rice roots inoculated and un-inoculated with FO-R20 strain in Example 2. +Cd means treatment with 5 µM cadmium, +CdF means insulation with FO-R20 and treatment with 5 µM cadmium. White arrows refers to cadmium ion fluorescence. The dye used is Leadmium™ Green AM dye, scale bar is 200 µm.

The cadmium fluorescent dye (Leadmium™ Green AM, Invitrogen, USA) was used for dyeing to analyze the difference of spatial distribution of the cadmium ions in the root systems of rice inoculated/un-inoculated with FO-R20. The result showed that in root systems of the rice (+Cd) un-inoculated with FO-R20, green fluorescent signals of cadmium ions were emitted through epidermal layer and endothelial layer cells, and particularly a large number of green fluorescent signals appeared in mesomere cells and vascular bundle cells (FIG. 6) and were transferred to overground tissues. In contrast, the green fluorescent signals in the root system of the rice (+CdF) inoculated with FO-R20 were scattered in the cortical cells and intercellular cells (FIG. 6), and the number of signals was obviously reduced. Therefore, the colonization of FO-R20 in the roots could reduce the cadmium ions in the roots of the rice.

Figure 7:
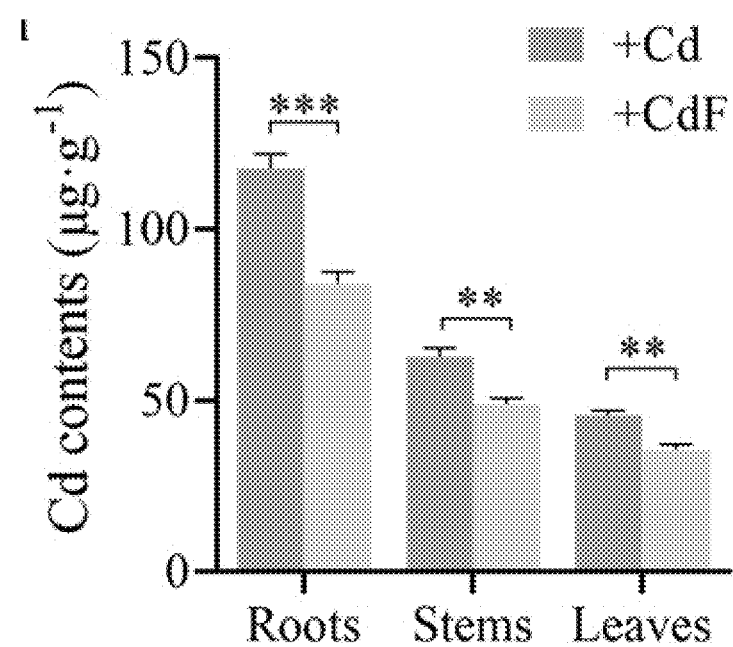
FIG. 7 shows effect of an FO-R20 strain on the cadmium content in different tissues of rice seedlings in Example 2. +Cd means 5 µM cadmium treatment, +CdF means insulation with FO-R20 and 5 µM cadmium treatment. The histogram shows mean±SD, n=3. Significance level (t test): *** means P<0.001.
Figure 8:
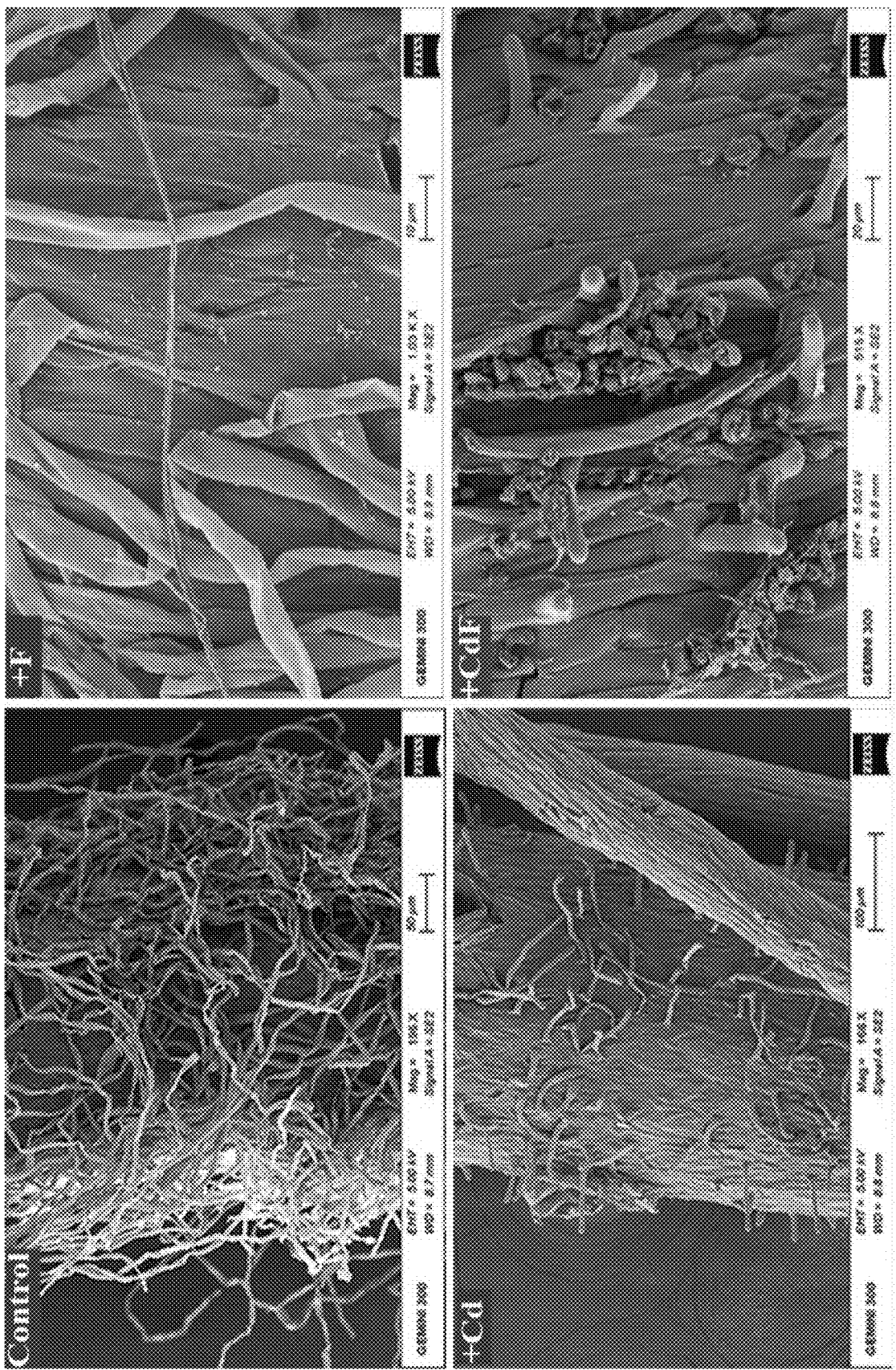
FIG. 8 shows colonization of an FO-R20 strain at roots of rice under a scanning electron microscope in Example 2 Root tissue is shown in green and fungal structures are shown in red. Control means control, +F means inoculation with FO-R20, +Cd means treatment with 5 µM, and +CdF means FO-R20 inoculation and treatment with 5 µM cadmium.
Figure 9:
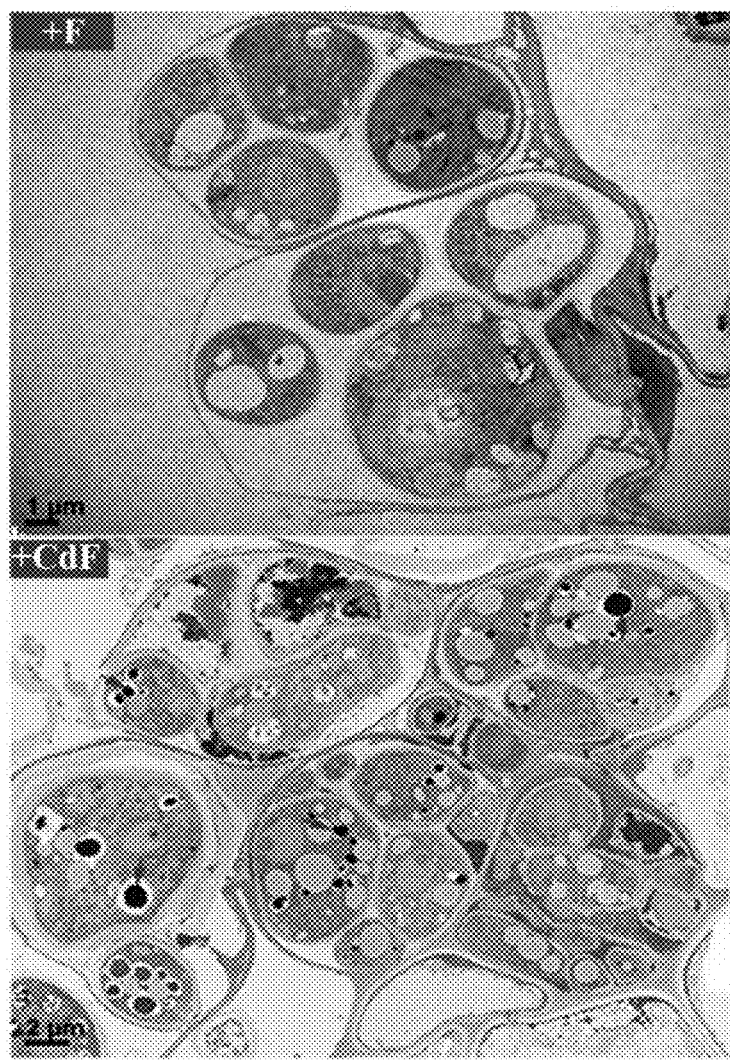
FIG. 9 is a picture of an FO-R20 strain adsorbing heavy metal cadmium in own mycelium under a transmission electron microscope in Example 2 Picture shows a cross section of root epidermal cells, cadmium accumulates in the large vacuoles of the mycelia. Red arrows refer to cadmium deposition. +F means inoculation with FO-R20, +CdF means inoculation with FO-R20 and treatment with 5 µM cadmium.

In the closed culture environment of the test tube, when the stress concentration of cadmium was 5 µM (namely 1.2 mg·kg$^{-1}$), the content of heavy metal cadmium in the roots and leaves of rice inoculated with FO-R20 was correspondingly and obviously lower than that of the control group (the content of heavy metal cadmium: root treatment<root control, stem treatment<stem control, and leaf treatment<leaf control) (FIG. 7). In a natural state, the FO-R20 was colonized in the root of the rice to form wandering mycelia. Under the stress of heavy metals, the FO-R20 forms a large number of microsclerosis structures at the root of the rice (FIG. 8). The observation under the transmission electron microscope showed that the FO-R20 adsorbed the heavy metal cadmium into vacuoles in the own mycelia (FIG. 9).

Figure 10:
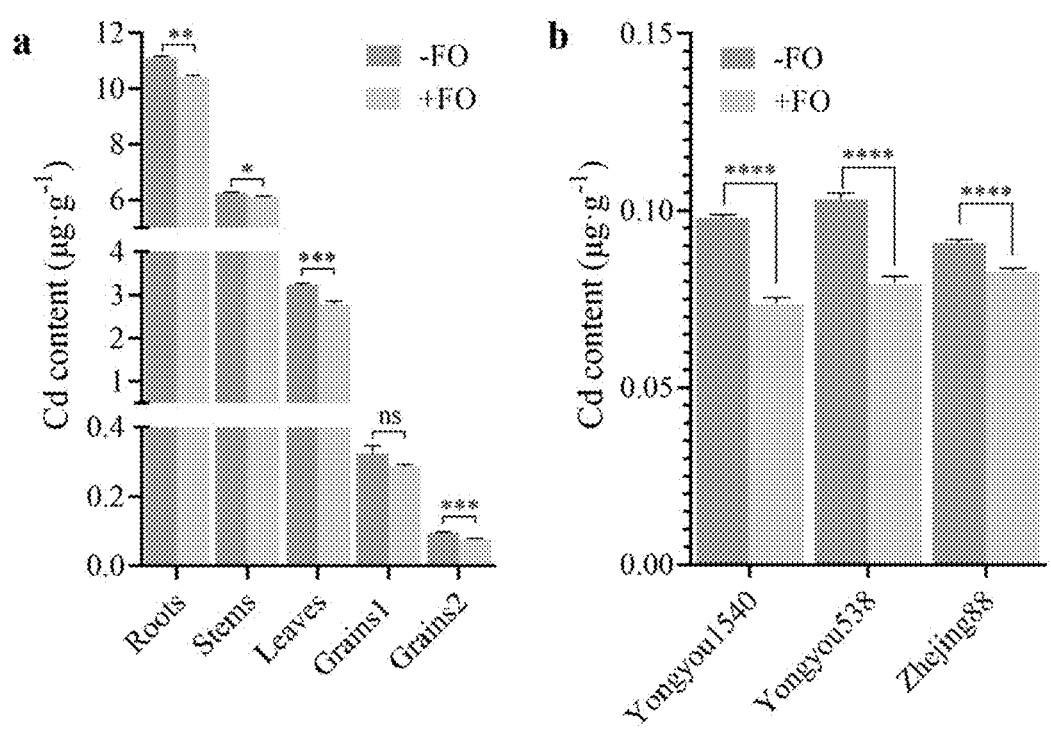
FIG. 10 shows an effect of an FO-R20 fungal fertilizer on reducing heavy metal cadmium in a field in Example 2. (a) FO-R20 fungal fertilizer reduces cadmium content in various tissues of rice in field, and the rice variety is Zhejing 88. The histogram shows mean±SD, n=3. (b) FO-R20 fungal fertilizer reduces cadmium content in grains of different rice varieties. The histogram shows mean±SD, n=4. Significant difference (t test): * means P<0.05,  means P<0.01, * means P<0.001, **** means P<0.0001, ns means no significance.

Under the condition of a natural field (the concentration of cadmium was 0.24 mg·kg$^{-1}$), the content of cadmium in the root systems, the stems, the leaves and the grains of the rice inoculated with the FO-R20 was still lower than that in the un-inoculated control group (FIG. 10). Moreover, the content of cadmium in each organ tissue was sequentially as follows: roots>stems>leaves>grains.

The invention claimed is:

1. A method of improving cadmium tolerance in rice comprising the steps of co-culturing the endophytic fungus *Falciphora oryzae* FO-R20 having the deposit number of CCTCC M 2021505 with rice seeds and colonizing the endophytic fungus *Falciphora oryzae* FO-R20 at the root tissue of rice.

2. A method of reducing cadmium content in rice grains comprising the steps of co-culturing the endophytic fungi *Falciphora oryzae* FO-R20 having the deposit number of CCTCC M 2021505 with rice seeds and colonizing the endophytic fungi *Falciphora oryzae* FO-R20 at the root tissue of rice.

3. A method for improving cadmium tolerance in rice and reducing cadmium content in rice grains, comprising the following steps:
   (a) inoculating the endophytic fungus *Falciphora oryzae* FO-R20 with the deposit number of CCTCC M 2021505 into a liquid fermentation medium and performing culturing to obtain fermentation broth, and then inoculating the fermentation broth on sterile barley grains and performing culturing in the dark until mycelia grow and the grains are covered with mycelia to obtain an FO-R20 solid fungal fertilizer;
   wherein the liquid fermentation medium contains 0.4% of soybean cake flour, 1% of corn flour, 0.05% of magnesium sulfate and 0.1% of dipotassium phosphate per 250 mL of the medium by mass;
   (b) mixing the FO-R20 solid fungal fertilizer with a seedling substrate to obtain a mixed substrate, in which germinated rice seeds are sown for seedling raising and culturing to obtain rice seedlings; and
   (c) transplanting the rice seedlings to a field, and performing culturing until harvest.

4. The method according to claim 3, wherein in the step (a), before liquid fermentation, the endophytic fungal *Falciphora oryzae* FO-R20 is inoculated in a PDA medium for activated culture and is cultured in dark for 7 days at 25° C.

5. The method according to claim 3, wherein in the step (a), the fermentation broth and the sterile barley grains are mixed in a ratio of 100 mL: 500 g, and the mixture is cultured at 25° C. in the dark until mycelia grow and the grains are covered with mycelia.

6. The method according to claim 3, wherein in the step (b) of preparing the mixed substrate, the solid fungal fertilizer and the seedling substrate are mixed in a mass ratio of 1:9.

7. The method according to claim 3, wherein in the step (b), the rice seeds are soaked in 3000-time diluted 25% phenamacril for 2 days for seed disinfection, and then placed in a dark constant-temperature incubator set at 30° C. for 1-2 days to facilitate germination.

* * * * *

SEQUENCE LISTING

<160> NUMBER OF SEQ ID NOS: 3

<210> SEQ ID NO 1
<211> LENGTH: 527
<212> TYPE: DNA
<213> ORGANISM: Falciphora oryzae

<400> SEQUENCE: 1

```
cggagggatc attaaagagt tgaaaaactc caacccctgt gaaccttacc tttactgttg      60
cttcggcgga cgacggccct tcgtggcccg aggccgccgg aggttccaaa ctctaaatct     120
ttagtgtatc tctgaggaaa ataaaccaat aattaaaact ttcaacaacg gatctcttgg     180
ttctggcatc gatgaagaac gcagcgaaat gcgataagta atgtgaattg cagaattcag     240
tgaatcatcg aatctttgaa cgcacattgc gcccgccggt attccggcgg gcatgcctgt     300
tcgagcgtca tttcaccact caagcccagc ttggtgttgg ggcacccggc cgcccggcgg     360
tcggggcccc caagtacatc ggcggtctcg ctaggaccct gagcgcagta actcgcggta     420
aaacgcgcct cgctcggaag ttcccagcgg gcttccagcc gctaaacccc ccctaatttt     480
cttaggttga cctcggatca ggtaggaata cccgctgaac ttaagca                  527
```

<210> SEQ ID NO 2
<211> LENGTH: 19
<212> TYPE: DNA
<213> ORGANISM: Artificial Sequence
<220> FEATURE:
<223> OTHER INFORMATION: Synthesized

<400> SEQUENCE: 2

```
tccgtaggtg aacctgcgg                                                   19
```

<210> SEQ ID NO 3
<211> LENGTH: 20
<212> TYPE: DNA
<213> ORGANISM: Artificial Sequence
<220> FEATURE:
<223> OTHER INFORMATION: Synthesized

<400> SEQUENCE: 3

```
tcctccgctt attgatatgc                                                  20
```